(12) United States Patent
Memar

(10) Patent No.: US 8,579,852 B2
(45) Date of Patent: Nov. 12, 2013

(54) APPARATUS AND METHODS FOR REPAIRING TISSUE DEFECTS

(76) Inventor: Omeed Memar, Chicago, IL (US)

( * ) Notice: Subject to any disclaimer, the term of this patent is extended or adjusted under 35 U.S.C. 154(b) by 582 days.

(21) Appl. No.: 12/708,685

(22) Filed: Feb. 19, 2010

(65) Prior Publication Data

US 2010/0152750 A1 Jun. 17, 2010

Related U.S. Application Data

(63) Continuation-in-part of application No. 11/531,930, filed on Sep. 14, 2006, now Pat. No. 7,771,754.

(51) Int. Cl.
*A61M 31/00* (2006.01)
*A47J 19/06* (2006.01)
*B02C 17/02* (2006.01)
*B07B 13/00* (2006.01)
*A47J 42/00* (2006.01)

(52) U.S. Cl.
USPC .............. 604/57; 604/59; 604/60; 604/62; 241/2; 241/93; 241/169.1

(58) Field of Classification Search
USPC .......... 604/59, 60, 57, 522, 62, 64; 241/2, 93, 241/169.1
See application file for complete search history.

(56) References Cited

U.S. PATENT DOCUMENTS

| | | | | |
|---|---|---|---|---|
| 4,212,430 A | * | 7/1980 | Dale et al. | 241/89.4 |
| 5,261,613 A | * | 11/1993 | Mullarky | 241/95 |
| 5,424,208 A | | 6/1995 | Lee et al. | |
| 6,582,438 B2 | * | 6/2003 | DeMayo | 606/92 |
| 2005/0173573 A1 | * | 8/2005 | Hay et al. | 241/199.12 |
| 2005/0216025 A1 | * | 9/2005 | Chern Lin et al. | 606/92 |

FOREIGN PATENT DOCUMENTS

WO WO 02/088296 11/2002

OTHER PUBLICATIONS

Alster et al., "Plastic & Reconstructive surgery," 105(7): 2515-2525 (2000).
Sclafani et al., *Arch Facial Plast Surg.*, 2: 130-136 (2000).
Pulverized, Definition from the Merriam-Webster Online Dictionary, Feb. 4, 2009.
Grinding, Definition from the Merriam-Webster Online Dictionary, Feb. 4, 2009.
Homogenized, Definition from the Merriam-Webster Online Dictionary, Feb. 4, 2009.

* cited by examiner

*Primary Examiner* — Bhisma Mehta
*Assistant Examiner* — Lauren M Peng
(74) *Attorney, Agent, or Firm* — Barnes & Thornburg, LLP; Mark J. Nahnsen

(57) ABSTRACT

Methods and devices to process harvested skin tissue and to immediately reintroduce the ground tissue into the patient to repair a tissue defect are disclosed. A hand-held portable tissue grinder comprising a housing and a grinding element are disclosed. The tissue grinder is used for grinding skin and subcutaneous tissue and includes a sterile polymer housing having a first opening adapted to receive the skin and subcutaneous tissue. The tissue grinder also includes a sterile grinding element disposed substantially within the housing. The grinding element includes a plurality of cutting surfaces adapted to operably engage with the housing to provide ground tissue and further includes a handle mechanism coupled to the grinding element to move the grinding element with respect to the housing to grind the skin and subcutaneous tissue, wherein the ground tissue can be removed from the housing.

12 Claims, 6 Drawing Sheets

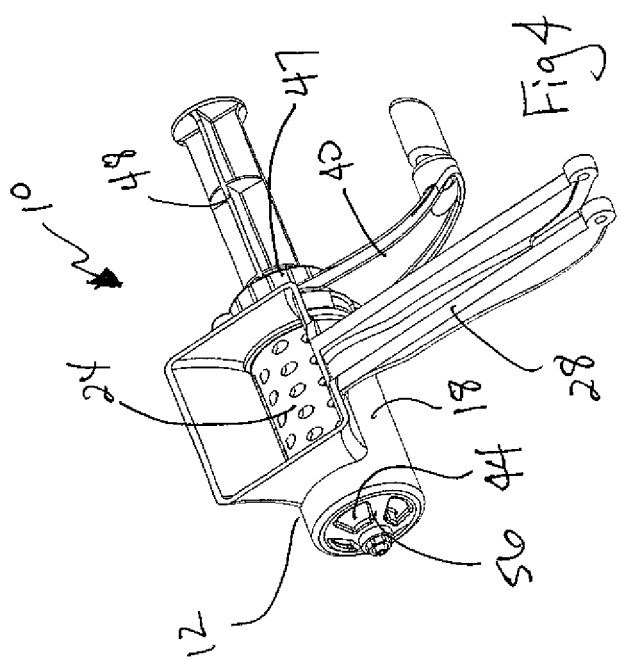

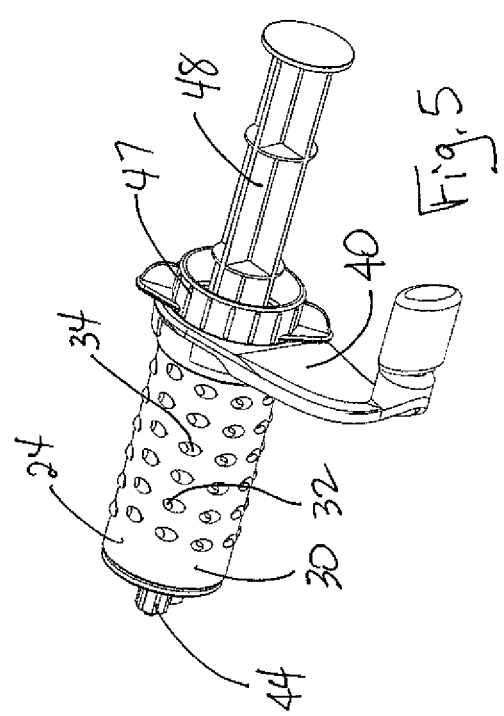

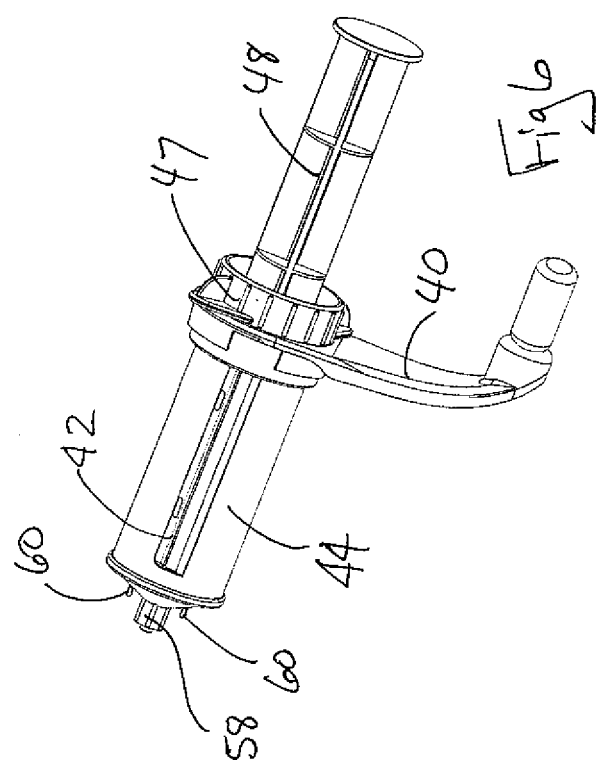

US 8,579,852 B2

APPARATUS AND METHODS FOR REPAIRING TISSUE DEFECTS

CROSS-REFERENCE TO RELATED APPLICATIONS

This application is a continuation-in-part of co-pending U.S. Ser. No. 11/531,930, filed Sep. 14, 2006 and is hereby incorporated by referenced in its entirety.

FIELD OF THE INVENTION

The present disclosure generally relates to devices and methods for repairing tissue defects. More particularly, the present disclosure relates to processing of harvested skin tissue, processing the skin tissue, reintroducing the processed skin tissue to a defective site, and repairing the defect.

BACKGROUND

Skin tissue generally comprises three distinct layers including the epidermis, the dermis, and the hypodermis or the sub-cutaneous layer.

The epidermis is the surface layer of the skin tissue and the thickness of the epidermis depends on a number of factors, including age, sex and the location on the body. For example, the skin on the bottom of the foot can be up to 30 cell-layers thick, while the skin on the eyelids is extremely thin. About 90 percent of the cells in the epidermis are keratinocytes, designated because they produce a characteristic fibrous protein called keratin, which provides many of the skin's protective properties. The bottom section of the epidermis, called the basal layer, contains melanocytes, which produce melanin—the skin pigment.

The dermis layer is positioned immediately beneath the epidermis and is connected by a continuous membrane. The dermis forms the thickest section of skin tissue and contains blood vessels, white blood cells, nerve endings, hair follicles, sweat glands and sebaceous glands. Fibroblasts constitute the main cell type in the dermis and they provide a source for collagen and elastin, the fibrous proteins that form the primary structural components of the skin tissue. The dermis provides moisture to the epidermis, produces collagen and elastin to maintain the structural integrity of the skin tissue, and contain glands that produce sebum to keep the skin supple and hydrated.

The hypodermis or the sub-cutaneous layer beneath the dermis, is composed of an extensive network of connective tissue and is imbued with fat cells. It acts as a protective cushion and helps to insulate the body by monitoring heat gain and heat loss. The sub-cutaneous or the hypodermis layer is some times not considered as part of the skin tissue.

Correction of tissue defects including functional, cosmetic, and aesthetic defects have primarily focused on injecting or implanting non-biological materials such as saline and silicone or processed biological materials such as isolated and cultured fibroblasts or other tissue cells. Introducing non-biological material or biological material derived from another source, for example, bovine collagen or cultured fibroblasts, may result in adverse reactions in the individual.

Therefore, there exists a need for simpler and practical procedures to repair tissue defects, including skin defects and for a device to process the tissue to enable repairing the defective tissue. The present disclosure provides methods to process a suitable tissue using a tissue grinder and to reintroduce the processed tissue to correct or repair the defective tissue site.

SUMMARY

The According to the present disclosure, a tissue grinder is used to process a suitable tissue from a suitable source from a patient such that the processed tissue is amenable for immediate reintroduction to a defective site on the patient for repairing the defect. A suitable tissue is for example, a skin tissue and a suitable source, for example, is an abdominal area of the patient in which the procedure is to be performed.

The method of repairing a defective tissue site includes the steps of obtaining a skin and subcutaneous tissue from a suitable source, removing a top epithelial component from the skin and the subcutaneous tissue and grinding the skin and subcutaneous tissue into constituents in a tissue grinder to provide a ground tissue, the tissue grinder comprising a cutting surface. The method also includes reintroducing the ground tissue to the defective site by directly applying the ground tissue at the defective site to repair the defective site.

The method incorporates the use of a surgical hand-held tissue grinder. The tissue grinder is used for grinding skin and subcutaneous tissue and includes a sterile polymer housing having a first opening adapted to receive the skin and subcutaneous tissue and a second opening in fluid connection with the first opening. The tissue grinder also includes a sterile grinder disposed within the housing. The grinder includes a grinding element provided with a plurality of cutting surfaces adapted to operably engage with the housing to provide ground tissue and further includes a handle mechanism coupled to the grinding element to move the grinding element with respect to the housing to grind the skin and subcutaneous tissue, wherein the ground tissue is deposited in a syringe for reintroduction into the patient.

The grinder assembly comprises a housing formed to include an inlet adapted to receive a material to be ground. The grinder assembly also includes a grinder having a cylindrical grinding element disposed within the housing, the grinding element formed to include a plurality of cutting surfaces adapted to grind the material. The grinder assembly includes a blade associated with the grinding element and configured to engage the grinding element to further cut the material ground by the grinding element. A handle mechanism is coupled to the grinding element to move the grinding element with respect to the housing and blade.

Additional features of the disclosure will become apparent to those skilled in the art upon consideration of the following detailed description of illustrative embodiments exemplifying the best mode of carrying out the disclosure as presently perceived.

BRIEF DESCRIPTION OF THE DRAWINGS

The present invention and the advantages thereof will become more apparent upon consideration of the following detailed description when taken in conjunction with the accompanying drawings of which:

FIG. 4 is a perspective view of the tissue grinder with the compression arm removed to reveal the grinding element of the grinder;

FIG. 5 is a perspective view of the grinder and the syringe positioned within the grinder; and FIG. 6 is a perspective view of the injection tube and plunger.

DETAILED DESCRIPTION

Figure 1:
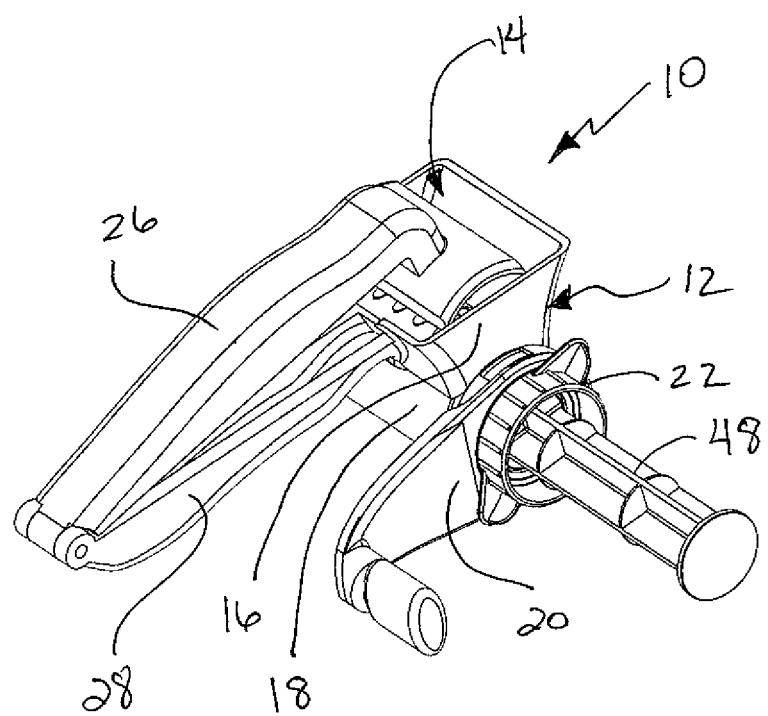
FIG. 1 is a perspective view of a hand held tissue grinder showing the housing, the grinder handle, and the plunger for the injection tube.

While the present disclosure may be susceptible to embodiment in different forms, there is shown in the drawings, and herein will be described in detail, embodiments with the understanding that the present description is to be considered an exemplification of the principles of the disclosure and is not intended to limit the disclosure to the details of construction and the arrangements of components set forth in the following description or illustrated in the drawings.

The disposable, surgical hand-held tissue grinder 10 is adapted for grinding skin and subcutaneous tissue for use in repairing tissue defects. The tissue grinder 10, as is shown in FIG. 1, includes a sterile polymer housing 12 having an inlet 14 for receiving tissue. The housing 12 includes a feed basket 16 for holding the tissue while it is being ground. The feed basket 16 is coupled to cylindrical chamber 18 that forms part of housing 12. Cylindrical chamber 18 is adapted to accept a sterile grinder 20 disposed within the cylindrical chamber 18. The tolerances between the grinding element 20 and the interior wall of cylindrical chamber 18 are in close proximity to one another. Sterile syringe 22 is positioned within grinder 20 and is configured to receive the tissue ground by grinder 20.

The housing 12 of hand-held tissue grinder 10 is dimensioned to be easily gripped by the hand of a medical practitioner to make it easy to operate the tissue grinder 10 during the medical procedure. Housing 12 is sterilized and is ready to be used by the medical practitioner from the packaging and can be discarded after the procedure is completed. Feed basket 16 is adapted to contain excised tissue prior to grinding. In order to force the tissue onto grinding element 24 of grinder 20, a compression arm 26 is used. Compression arm 26 is preferably hingedly coupled to handle 28 of housing 12. Housing 12 is preferably made from a polymer material so that it can be disposed of after use. Housing 12, shown in the illustrative embodiment of FIG. 2, includes an open end 46 that is adapted to accept grinder 20 and syringe 22.

Figure 2:
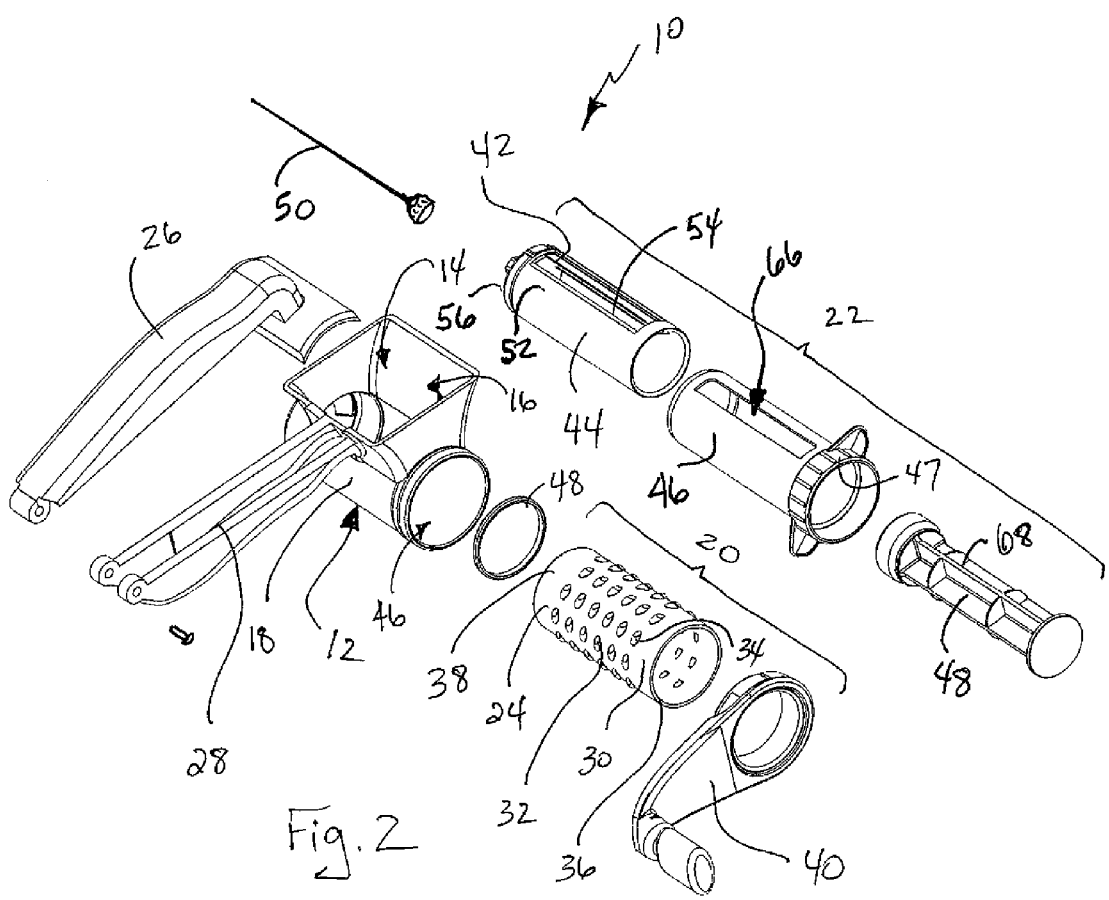
FIG. 2 is an exploded view of the tissue grinder.

Sterile grinding element 24 is configured to be disposed substantially within housing 12, as shown in FIGS. 1 and 2. Sterile grinding element 24 is preferably cylindrical and includes a cylindrical wall 30. The diameter of cylindrical wall 30 is less than the diameter of cylindrical chamber 18 such that grinding element 24 can rotate with respect to housing 12. Grinding element 24 also includes a plurality of openings 32 that include cutting surfaces 34 in the form of sharpened edges at the edge of openings 32.

Grinding element 24 includes a first end 36 and a spaced apart second end 38, as shown in FIG. 2. First end 36 of grinding element 24 is connected to handle 40 which is used to rotate grinding element 24 with respect to housing 12. Rotation of handle 40 causes rotation of grinding element 24 inside of housing 12. When tissue positioned within inlet 14 is forced downward against grinding element 24, cutting edges 34 of grinding element 24 engage and cut tissue which is then deposited through openings 30 into syringe 22.

Figure 3:
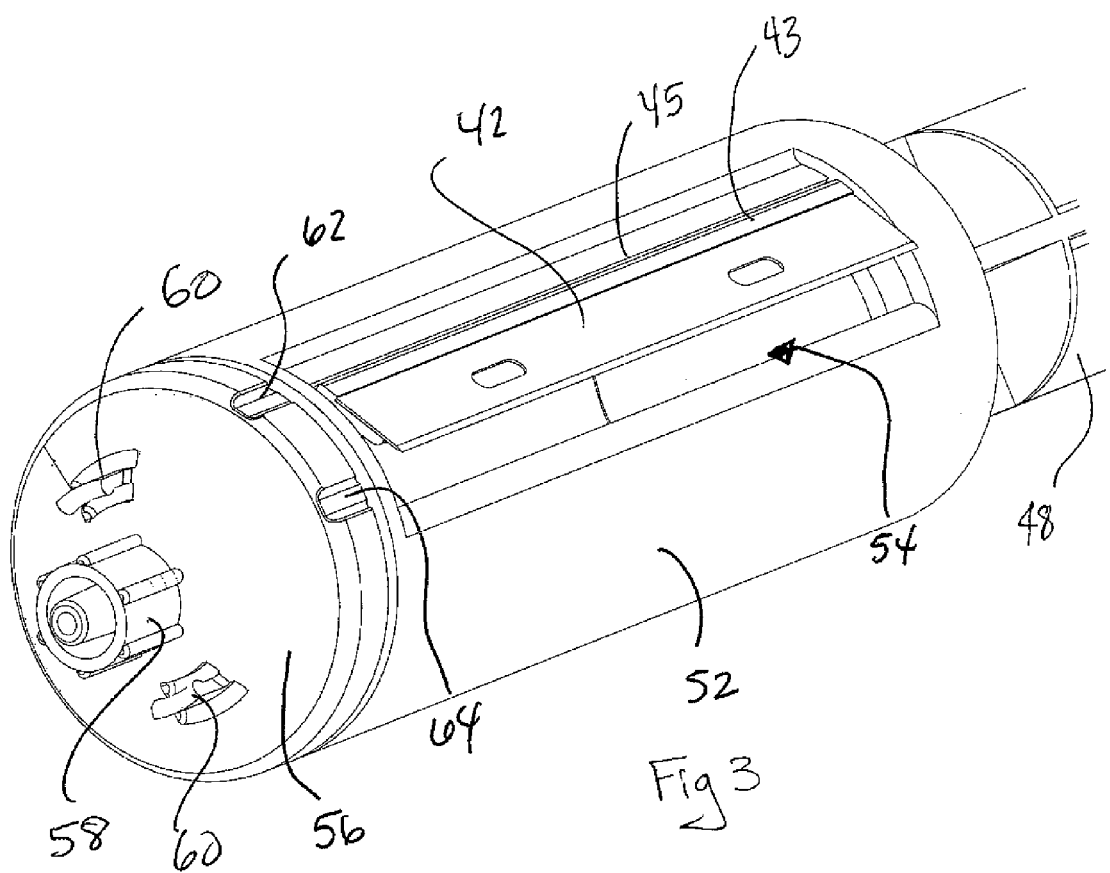
FIG. 3 is an enlarged perspective view of the injection tube of the syringe showing the retention clips for securing the injection tube to the housing and a blade that cuts tissue a second time and directs the tissue into the injection tube.

Cut tissue that passes through openings 30 is cut a second time by blade 42 of injection tube 44 of syringe 22, as shown, in FIGS. 2 and 3. Blade 42 of injection tube 44 engages the inside surface of grinding element 24 to cut and direct the tissue to inside the injection tube 44 of syringe 22. Housing includes one or more seals 48 that seal grinder 20 to housing 12. Blade 42 is mounted on flap 43 of injection tube 44. While blade 42 is used in connection with the tissue grinder, it is contemplated that the blade 42 may be used in non-tissue grinders to further reduce the size of the material ground by the grinder, such as food grade grinders. Flap 43 includes a living hinge 45 that biases blade 42 outwardly but allows blade 42 to move inwardly when syringe sleeve 46 is moved to a second position to cover blade 42 and opening 54.

Syringe 22 is configured to be positioned within grinder 20, as shown in FIG. 5. Syringe 22 includes injection tube 44, a two position syringe sleeve 46 and a plunger 48. Injection tube 44 is configured to accept needle 50 and receives tissue ground by grinder 20. Injection tube 44 includes a cylindrical wall 52 formed to include opening 54. Cylindrical wall 52 also includes blade 42 which is used to regrind and direct tissue into injection tube 44. Injection tube 44 also includes a front wall 56 that accepts needle 50 by use of fitting 58. Front wall 56 also includes clips 60 that engage and retain injection tube 44 to housing 12. The clips 60 also allow injection tube 44 to removed from housing 12.

Cylindrical wall 52 also includes detents 62, 64 that allow two position syringe sleeve 46 to be locked from a first position where slot 66 is aligned with slot 54 of injection tube 44 so that blade 42 can extend through slot 66 to a second position where slot 66 is not aligned with injection tube 44 and covers blade 42. In the second position, plunger 48 can be moved through injection tube 44 to compress the ground tissue so that it exits needle 50. Syringe sleeve 46 includes collar 47 to allow a user to rotate syringe sleeve 46 with respect to injection tube 44 from the first position to the second position. Syringe sleeve 46 is designed to protect the user from blade 42 and to seal opening 54 so that ground tissue can be ejected from needle 50.

Plunger 48 is adapted to fit within injection tube 44. Plunger 48 includes shaft 68 that allows plunger 48 to be pushed within injection tube 44. In use, the user removes a sterilized hand-held tissue grinder 10 from a sealed bag or container. With the hand-held tissue grinder 10 fully assembled, the user excises tissue from the patient and inserts the tissue in the feed basket 14. Once tissue is in feed basket 14 handle 26 is squeezed to force tissue onto grinder element 24. With tissue positioned against grinder element 24, handle 40 is rotates to cause cutting surfaces 34 to cut tissue.

While handle 40 and cutting element 24 rotate within housing 12, syringe 22 does not rotate, which allows blade 42 to engage inside surface of cutting element 24 to cut tissue for a second time and direct tissue into injection tube 44. Once a sufficient amount of tissue is ground to repair a defect in a patient and deposited inside of injection tube 44, syringe 22 is removed from housing 12. Once removed from housing 12, syringe sleeve 46 is rotated from the first position to a second position to cover blade 42 and opening 54. Once opening 54 is covered, needle 50 is installed on injection tube 44 and plunger 48 is pressed inwardly to eject ground tissue from needle 50.

In an embodiment, a suitable tissue such as, for example, a skin and subcutaneous tissue is obtained from a suitable source of the individual with a tissue defect. As used herein, "skin and subcutaneous tissue" generally refers to the skin tissue comprising the epidermis, the dermis and the hypodermis or the layer beneath the dermis layer. In addition, the term "skin tissue" generally refers to the epidermal and the dermal layers. For example, a suitable source to obtain the skin and subcutaneous tissue is lower abdominal area. Other suitable sources include thigh, buttocks, and any bodily region capable of providing an adequate amount of the skin and subcutaneous tissue.

Any tissue that can be ground and reintroduced to repair a tissue defect or augment the structural or functional integrity of a tissue is within the scope of this disclosure.

The skin and subcutaneous tissue is removed from the suitable source by employing any suitable technique that is practiced in the art. For example, the skin and subcutaneous tissue is obtained from the abdominal region by surgically excising the desired tissue from the source. The nature and the amount of the tissue depends on the nature of the defect and the extent of the defect to be repaired and the availability of suitable tissue at the source. For example, a tissue defect includes a facial defect. The tissue defect can be functional, cosmetic or a combination thereof. Some examples of tissue defects includes, for example wrinkles, altering of facial contours and scar correction. It is preferable to obtain the tissue from the same individual for whom the tissue defect is corrected.

In an embodiment, after the tissue is obtained from the suitable source, the skin tissue is processed by removing an epithelial component or the epidermal layer of the skin tissue. Epithelial components include, such as, for example, keratinocytes, dendritic cells, melanocytes, hair follicles and squamous cell. It is preferable to substantially remove the hair follicles and other undesirable constituents prior to reintroduction of the ground tissue to the defective tissue site. The epithelial component is removed using any standard methods available in the art. For example, an epithelial component is removed by mechanical force. Other modes of removal, such as, for example, chemical and biological treatments can also be used to remove or substantially reduce the prevalence of an epithelial component in the harvested skin and subcutaneous tissue.

After an appropriate amount of the skin and subcutaneous tissue has been processed, the processed tissue is subject to a grinding force in a tissue grinder. In an embodiment, the grinding force is a torque applied by a grinding element of the grinder. In an embodiment, the grinding element includes cutting surface that has a plurality of openings. Other forms of mechanical action, in addition to the rotational torque is suitable. For example, horizontal sliding movement of the grinding element is also suitable for operating the tissue grinder to provide a ground tissue. Briefly, the harvested tissue is transferred to the tissue grinder through an opening in the housing of the grinder. Optionally, the tissue is held against the grinding element by force such that the grinding element engagedly contacts the tissue. The grinding element is operated such that the movement of the grinding element with respect to the housing grinds the tissue. The ground tissue is collected and transferred to another suitable device, e.g., a syringe to be introduced into the defective tissue site.

In an embodiment the skin and subcutaneous tissue is ground by the grinder such that the ground tissue has constituents that range in size from about 50 .mu.m to about 5000 .mu.m in diameter. The constituents can also range in size from about 100 .mu.m to about 1000 .mu.m; and from about 500 .mu.m to about 3000 .mu.m. The ground tissue includes skin constituents that range in size that are slightly bigger than the size of an individual cell to about 10-100 times bigger than the size of the individual cell. The ground skin and subcutaneous tissue contains aggregates of cells that are capable of providing support for growth and establishment of the implanted tissue and correct the tissue defect. For example, fat cells and blood vessels that form a part of the dermal layer and the subcutaneous layer provide nourishment to support the growth of the skin tissue fat immediately surrounds the implanted tissue.

After the tissue is ground, optionally the tissue is transferred to a suitable applicator device, such as, for example, a syringe. The ground tissue is then directly administered at a defective site. In an embodiment, the ground tissue is injected or applied beneath the existing skin and subcutaneous tissue to correct the defect. The ground tissue can be applied under or over any layer as long as the implanted ground tissue (graft) is accepted by the surrounding tissue (host). The ground tissue can also be applied directly on a defective site with any suitable applicator. An incision can be made at the defective site to permit effective implantation of the ground tissue. After the implantation, appropriate surgical measures, such as, suturing and bandaging the defective site, are adopted as necessary.

In another embodiment, the tissue grinder is adapted to functionally engage the applicator device so that the tissue removal and transfer step is eliminated. In yet another embodiment, the tissue grinder itself comprises an applicator member capable of transferring the ground tissue to the defective site.

While embodiments have been illustrated and described in the drawings and foregoing description, such illustrations and descriptions are considered to be exemplary and not restrictive in character, it being understood that only illustrative embodiments have been shown and described and that all changes and modifications that come within the spirit of the disclosure are desired to be protected. The description and figures are intended as illustrations of embodiments of the disclosure, and are not intended to be construed as having or implying limitation of the disclosure to those embodiments.

There are a plurality of advantages of the present disclosure arising from various features set forth in the description. It will be noted that alternative embodiments of the disclosure may not include all of the features described yet still benefit from at least some of the advantages of such features. Those of ordinary skill in the art may readily devise their own implementations of the disclosure and associated methods, without undue experimentation, that incorporate one or more of the features of the disclosure and fall within the spirit and scope of the present disclosure and the appended claims.

The claimed invention is:

1. A disposable surgical hand-held tissue grinder for grinding skin and subcutaneous tissue comprising:
   a sterile polymer housing formed to include an inlet adapted to receive the skin and subcutaneous tissue;
   a sterile grinder having a grinding element generally disposed within the housing, the grinding element including a plurality of cutting surfaces adapted to wind the skin and subcutaneous tissue to provide a ground tissue; and
   a handle mechanism coupled to the grinding element to rotate the grinding element about an axis of rotation with respect to the housing to grind the skin and subcutaneous tissue;
   a sterile container positioned within the grinder, the container configured to receive the ground tissue, wherein the container can be removed from the grinder to allow the ground tissue to be used;
   wherein, the sterile container includes an injection tube that includes a sidewall formed to include an opening configured to receive the ground tissue, and wherein the sterile container includes a plunger configured to move linearly along the axis of rotation within the injection tube to discharge the ground tissue from one end of the sterile container.

2. The tissue grinder of claim 1, wherein the grinding element imparts a torque against the tissue.

3. The tissue grinder of claim 1, further including a syringe sleeve positioned between the grinding element and the injection tube, the syringe sleeve having a side wall formed to include an opening, wherein when the syringe sleeve is in a first position ground tissue can enter the injection tube and when the syringe sleeve is in a second position, ground tissue cannot enter the injection tube.

4. The tissue grinder of claim 3, wherein the injection tube includes a blade.

5. The tissue grinder of claim 4, wherein the blade extends through the opening of the syringe sleeve in the first position and is covered by the syringe sleeve in the second position.

6. A sterile surgical hand-held tissue grinder for grinding skin and subcutaneous tissue comprising:
   a sterile polymer housing formed to include an inlet adapted to receive the skin and subcutaneous tissue;
   a sterile grinder having a grinding element disposed substantially within the housing, the grinding element including a plurality of cutting surfaces adapted to operably engage with the housing to provide a ground tissue; and
   the grinding element configured to be rotated with respect to the housing about an axis of rotation to grind the skin and subcutaneous tissue;
   a syringe positioned within the grinder, the syringe configured to receive the ground tissue from the grinding element, wherein the syringe can be removed from the grinder to allow the ground tissue to be used;
   wherein the syringe includes an injection tube that includes a sidewall formed to include an opening configured to receive the ground tissue, and wherein the syringe includes a plunger configured to move linearly along the axis of rotation within the injection tube to discharge the ground tissue from one end of the syringe.

7. The tissue grinder of claim 6, wherein the grinding element imparts a torque against the tissue.

8. The tissue grinder of claim 6, further including a syringe sleeve positioned between the grinding element and the injection tube, the syringe sleeve having a side wall formed to include an opening, wherein when the syringe sleeve is in a first position ground tissue can enter the injection tube and when in a second position, ground tissue cannot enter the injection tube.

9. The tissue grinder of claim 8, further including a plunger configured to move within the injection tube.

10. The tissue grinder of claim 8, wherein the injection tube includes a blade.

11. The tissue grinder of claim 8, wherein the blade extends through the opening of the syringe sleeve in the first position and is covered by the syringe sleeve in the second position.

12. The tissue grinder of claim 11, wherein the blade is configured to engage the grinding element to further cut the skin and subcutaneous tissue ground by the grinding element.

\* \* \* \* \*